(12) United States Patent
De Keyzer et al.

(10) Patent No.: US 6,657,000 B1
(45) Date of Patent: Dec. 2, 2003

(54) HOT MELT PRESSURE SENSITIVE POSITIONING ADHESIVE (III)

(75) Inventors: Noël Raymond Maurice De Keyzer, Ottignies (BE); Carolyn Ann Stoner, Houston, TX (US)

(73) Assignee: Kraton Polymers U.S. LLC, Houston, TX (US)

( * ) Notice: Subject to any disclaimer, the term of this patent is extended or adjusted under 35 U.S.C. 154(b) by 437 days.

(21) Appl. No.: 09/597,207

(22) Filed: Jun. 20, 2000

Related U.S. Application Data

(60) Provisional application No. 60/141,146, filed on Jun. 25, 1999.

(51) Int. Cl.$^7$ ............................................... C08L 53/00
(52) U.S. Cl. ..................... 524/505; 524/270; 524/274; 524/515; 524/528
(58) Field of Search ................................ 524/270, 274, 524/505, 515, 528

(56) References Cited

U.S. PATENT DOCUMENTS

| | | | |
|---|---|---|---|
| 5,591,792 A | * | 1/1997 | Hattori et al. ............... 524/571 |
| H1808 H | * | 10/1999 | Djiauw et al. ............... 524/505 |

FOREIGN PATENT DOCUMENTS

| | | | |
|---|---|---|---|
| WO | WO 89/01002 | | 2/1989 |
| WO | WO 97/33921 | * | 9/1997 |
| WO | WO 98/15407 | | 4/1998 |
| WO | WO 99/37730 | | 7/1999 |
| WO | WO 00/00565 | * | 1/2000 |

OTHER PUBLICATIONS

International Search Report of Nov. 22, 2000.

* cited by examiner

*Primary Examiner*—Peter D. Mulcahy

(57) ABSTRACT

The present invention is a hot melt pressure sensitive positioning adhesive for use with an absorbent article. The adhesive comprises:

(a) from 5 to less than 15 percent by weight of a blend of
  (i) a hydrogenated styrene-(butadiene or isoprene)-styrene block copolymer having a polystyrene block number average molecular weight of 20,000 or less, and
  (ii) a homogeneous linear or substantially linear interpolymer of ethylene and at least one $C_3$–$C_{20}$ alpha olefin having a density from 0.85 to 0.91 grams per cubic centimeter; and
(b) from 50 to 80 percent by weight of a tackifying resin which has an aromaticity such that the MMAP cloud point is at least 45° C.; and
(c) from 5 to 35 percent by weight of a plasticizing oil.

The block copolymer of (i) may also be one in which the polystyrene block molecular weight is greater than 20,000. In such case, the tackifying resin must have an aromaticity wherein the MMAP cloud point is at least 70° C.

18 Claims, No Drawings

HOT MELT PRESSURE SENSITIVE POSITIONING ADHESIVE (III)

This application claims the benefit of U.S. Provisional Application No. 60/141,146, filed Jun. 25, 1999, the entire disclosure of which is hereby incorporated by reference.

FIELD OF THE INVENTION

This invention relates to hot melt pressure sensitive positioning adhesives for use with absorbent articles which are based on hydrogenated block copolymers of styrene and butadiene and/or isoprene. More particularly, the invention relates to such adhesives which incorporate interpolymers of ethylene and at least one $C_3$–$C_{20}$ alpha olefin for improved viscosity and viscosity/temperature profile.

BACKGROUND OF THE INVENTION

Positioning adhesives are used on disposable articles (absorbent articles) such as sanitary napkins, incontinent pads, bed pads, feminine pads, panty shields, diaper inserts, etc. where an adhesive layer is used to attach the article to a woven fabric substrate such as a supporting undergarment or bed sheet. The positioning adhesive is commonly applied to a release liner and transfer coated to the garment facing surface of the disposable article. The positioning adhesive must be capable of attaching to the undergarment to hold the article in place without transferring to or otherwise being deposited on the undergarment. Furthermore, the adhesive must not discolor, damage, or disturb the fibers of the garment.

The positioning adhesive must be a pressure sensitive adhesive that has a viscosity that permits it to readily flow onto and partially penetrate the particular surface to which it is applied. It must have good bond strength and high tack for initial placement of the article on the undergarment but also must have the ability to avoid loss of adhesion over time due to temperature and low pressure conditions. Finally, these articles are sometimes used for long periods of times at body temperature and they can have the drawback that the hot melt adhesive gradually softens and penetrates into the undergarment to which the article is adhering. In this case, the adhesive force greatly increases and the cohesive force is reduced. This causes the adhesive layer to suffer cohesion breakdown when the article is removed and some adhesive remains on the undergarment. Prevention of this deposit of adhesive on the undergarment is accordingly a necessary prerequisite for a successful positionable hot melt adhesive composition.

Block copolymers of styrene and dienes such as butadiene or isoprene have been used for a number of years in positionable hot melt adhesive formulations. More recently, the material of choice for such adhesives in feminine care applications has been hydrogenated block copolymers of styrene and butadiene such as KRATON® G1650 SEBS (hydrogenated styrene-butadiene-styrene) block copolymer. Formulations based on these SEBS block copolymers have been found to have excellent adhesion to fabrics like cotton and nylon and have the advantage that they leave no residue after peeling. The application viscosity of formulations using these polymers is acceptable but it would be advantageous to have a positionable adhesive formulation which has a lower viscosity in order to lower the application temperature. This reduces the risk of degradation, char forming, and filter plugging. This also results in energy and cost savings, decreases maintenance costs, and reduces the amount of odor due to the volatiles coming from the adhesive. The present invention provides such an improved positionable hot melt adhesive formulation.

SUMMARY OF THE INVENTION

The present invention is a hot melt pressure sensitive positioning adhesive for use with an absorbent article. The adhesive comprises:

(a) from 5 to less than 15 percent by weight, basis the total of (a), (b), and (c), of a blend of
   (i) a hydrogenated styrene-(butadiene or isoprene)-styrene block copolymer having a polystyrene block molecular weight of 20,000 or less, and
   (ii) a homogeneous linear or substantially linear interpolymer of ethylene and at least one $C_3$–$C_{20}$ alpha olefin having a density from 0.85 to 0.91 grams per cubic centimeter; and (b) from 50 to 80 percent by weight, basis the total of (a), (b), and (c), of a tackifying resin which has an aromaticity such that the MMAP cloud point is at least 45° C.; and (c) from 5 to 35 percent by weight, basis the total of (a), (b), and (c), of a plasticizing oil.

The weight ratio of the block copolymer and the interpolymer in (a) may range from 90:10 to 10:90, preferably from 80:20 to 20:80, more preferably from 60:40 to 40:60. In the case where the polystyrene block number average molecular weight is from 5500 to 9500 and the total number average molecular weight is from 65,000 to 95,000, the weight ratio may range from 60:40 to 90:10, preferably 80:20 to 90:10. The block copolymer of (i) may also be one in which the polystyrene block molecular weight is greater than 20,000. In such case, the tackifying resin must have an aromaticity wherein the MMAP cloud point is at least 70° C. In each embodiment, a second block copolymer can be added to the block copolymer of (i) to lower the viscosity. One option is to add a second polymer which has a diblock content of 20 to 70 percent by weight. A second option, irrespective of diblock content is if the base hydrogenated styrene-butadiene or isoprene-styrene block copolymer has a polystyrene content of 25 percent by weight or more, preferably 30 percent by weight or more, the polymer which is added to it to decrease the viscosity has a polystyrene content of less than 25 percent by weight, preferably 22 percent by weight or less.

Another option is to add more than two block copolymers. For example, a blend of a styrenic triblock copolymer, plus a styrenic block copolymer containing diblock, and a styrenic block copolymer containing less than 25% polystyrene could be used. Additionally, styrenic diblock copolymers could be added or copolymers with an ethylene/propylene multiblock could be added. This list is not limitative and therefore, it can be appreciated that a wide variety of block copolymers are useful in this invention including ABA triblock structures, ABA/AB triblock/diblock structures, AB diblock structures, $(B)_n$ structures, ABAB tetrablock structures where the A endblock is a non-elastomeric polymer block, typically polystyrene, and B is ethylene/butylene (hydrogenated butadiene) or ethylene/propylene (hydrogenated isoprene). Also included in the list are polymers which are grafted with maleic anhydride.

DETAILED DESCRIPTION OF THE INVENTION

One of the primary components of the positioning adhesive composition of the present invention is the above-described hydrogenated block copolymer which has two polystyrene endblocks and a saturated or hydrogenated polybutadiene and/or polyisoprene midblock. This conventional hydrogenated base block copolymer provides the primary load bearing capability of the adhesive composition. It is important that the polymer be hydrogenated so that the structural integrity of the polymer is preserved even if outside forces that cause degradation are encountered. The block copolymer may be hydrogenated as generally described in the prior art, preferably so as to reduce at least 90 percent of any olefinic double bonds in the polymer chains. Suitably at least 50 percent, preferably at least 70 percent, and more preferably at least 90 percent, most preferably at least 95 percent of the original olefinic unsaturation is hydrogenated.

The butadiene (isoprene) used in this invention should be one which forms a polybutadiene (polyisoprene) block which is largely amorphous at use temperatures (usually body temperature) and does not contain excess crystallinity which would interfere with flexibility. For hydrogenated polybutadiene blocks, it is generally best that the vinyl content before hydrogenation not be less than 18 percent by weight, preferably not less than 30 20 percent by weight because below that number, the crystallinity of the polymer is too high, giving a stiff polymer which is unsuitable for use in pressure sensitive adhesives.

The term "vinyl content before hydrogenation" refers to the fact that a conjugated diene is polymerized via 1,2-addition (in the case of butadiene—it would be 1,2-addition or 3,4-addition in the case of isoprene). Although a pure "vinyl" group is formed only in the case of 1,2-addition polymerization of 1,3-butadiene, the effects of 3,4-addition polymerization of isoprene (and similar addition for other conjugated dienes) on the final properties of the block copolymer will be similar. The term "vinyl" refers to the presence of a pendant vinyl group on the polymer chain. The purpose here is to introduce chain branching and to reduce the size of the main polymer backbone (since some of the carbons in the diene are in the pendant group) which reduces the end to end length of the molecule and, in turn, its viscosity in the cement.

Anionic polymerization of conjugated diene hydrocarbons with lithium initiators is well known as described in U.S. Pat. Nos. 4,039,593 and Re. 27,145 which descriptions are incorporated herein by reference. Polymerization commences with a monolithium, dilithium, or polylithium initiator which builds a living polymer backbone at each lithium site. Typical living polymer structures containing polymerized conjugated diene hydrocarbons are:

X-B-Li

X-A-B-Li

X-A-B-A-Li

Li-B-Y-B-Li

Li-A-B-Y-B-A-Li wherein B represents polymerized units of one or more conjugated diene hydrocarbons such as butadiene or isoprene, A represents polymerized units of one or more vinyl aromatic compounds such as styrene, X is the residue of a monolithium initiator such as sec-butyllithium, and Y is the residue of a dilithium initiator such as the diadduct of sec-butyllithium and m-diisopropenylbenzene. Some structures, including those pertaining to polylithium initiators or random units of styrene and a conjugated diene, generally have limited practical utility although known in the art.

The anionic polymerization of the conjugated diene hydrocarbons is typically controlled with structure modifiers such as diethylether or ethyl glyme (1,2-diethoxyethane) to obtain the desired amount of 1,2-addition (vinyl content). As described in Re 27,145 which is incorporated by reference herein, the level of 1,2-addition of a butadiene polymer or copolymer can greatly affect elastomeric properties after hydrogenation. The 1,2-addition of butadiene polymers significantly and surprisingly additionally influences the polymer as described above. A 1,2-addition of about 40% may be achieved during polymerization at 50° C. with about 6% by volume of diethylether or about 200 ppm of ethyl glyme in the final solution. A 1,2 addition of about 47% may be achieved during polymerization by the presence of about 250 ppm of ortho-dimethoxybenzene (ODMB) in the final solution. A 1,2 addition of 78% may be achieved during polymerization by the presence of about 300 ppm of 1,2-diethoxypropane (DEP) in the final solution.

In general, the polymers useful in this invention may be prepared by contacting the monomer or monomers with an organoalkali metal compound in a suitable solvent at a temperature within the range from −150° C. to 300° C., preferably at a temperature within the range from 0° C. to 100° C. Particularly effective polymerization initiators are organolithium compounds having the general formula:

RLi wherein R is an aliphatic, cycloaliphatic, alkyl-substituted cycloaliphatic, aromatic or alkyl-substituted aromatic hydrocarbon radical having from 1 to 20 carbon atoms.

Suitable solvents include those useful in the solution polymerization of the polymer and include aliphatic, cycloaliphatic, alkyl-substituted cycloaliphatic, aromatic and alkyl-substituted aromatic hydrocarbons, ethers and mixtures thereof. Suitable solvents, then, include aliphatic hydrocarbons such as butane, pentane, hexane, heptane and the like, cycloaliphatic hydrocarbons such as cyclohexane, cycloheptane and the like, alkyl-substituted cycloaliphatic hydrocarbons such as methylcyclohexane, methylcycloheptane and the like, aromatic hydrocarbons such as benzene and the alkyl-substituted aromatic hydrocarbons such as toluene, xylene and the like and ethers such as tetrahydrofuran, diethylether, di-n-butyl ether and the like.

The hydrogenation of these polymers may be carried out by a variety of well established processes including hydrogenation in the presence of such catalysts as Raney Nickel, noble metals such as platinum, palladium and the like and soluble transition metal catalysts. Suitable hydrogenation processes which can be used are ones wherein the diene-containing polymer or copolymer is dissolved in an inert hydrocarbon diluent such as cyclohexane and hydrogenated by reaction with hydrogen in the present of a soluble hydrogenation catalyst. Such processes are disclosed in U.S. Pat. Nos. 3,113,986, 4,226,952 and Reissue 27,145, the disclosures of which are herein incorporated by reference. The polymers are hydrogenated in such a manner as to produce hydrogenated polymers having a residual unsaturation content in polydiene blocks of less than about 1 percent, and preferably as close to 0 percent as possible, of their original unsaturation content prior to hydrogenation. A titanium catalyst such as disclosed in U.S. Pat. No. 5,039,755, which is herein incorporated by reference, may also be used in the hydrogenation process.

The molecular weights of linear polymers or unassembled linear segments of polymers such as mono-, di-, triblock, etc., or the arms of star polymers before coupling are conveniently measured by Gel Permeation Chromatography (GPC), where the GPC system has been appropriately calibrated with polystyrene homopolymer standards (ASTM D3536). For anionically polymerized linear polymers, the polymer is essentially monodisperse (weight average molecular weight/number average molecular weight ratio approaches unity), and it is both convenient and adequately descriptive to report the "peak" molecular weight of the narrow molecular weight distribution observed. Usually, the peak value is between the number and the weight average. The peak molecular weight is the molecular weight of the main species shown on the chromatograph. For polydisperse polymers the weight average or number average molecular weight is calculated from the chromatograph and used. The materials used in the columns of the GPC are styrene-divinyl benzene gels or silica gels. The solvent is tetrahydrofuran and the detector is a refractive index detector.

As discussed above, the adhesive of the present invention contains from 5 to less than 15 percent by weight of a blend of a block copolymer of styrene and butadiene and/or isoprene and a homogeneous linear or substantially linear interpolymer of ethylene and a $C_3$–$C_{20}$ alpha olefin. At least 5 percent is necessary to get the desired pressure sensitive adhesive properties and for the adhesive to be sufficiently cohesive. It is preferred that the maximum amount of the blend be less than 15 percent by weight in order to keep the viscosity of the adhesive sufficiently low for the positioning adhesive application. More polymer than 15 percent can be used and good adhesion properties will be obtained but the viscosity will be unnecessarily increased.

For block copolymers having a polystyrene block number average molecular weight of above 9500 and a total number average molecular weight of above 95,000 to 300,000, the block copolymer and interpolymer in the blend may be used in a weight ratio of 90:10 to 10:90. It is preferred that the weight ratio range be from 20:80 to 80:20. A weight ratio range of 60:40 to 40:60 is most preferred because the best combination of properties is achieved in this range. For block copolymers having a polystyrene block number average molecular weight of 5500 to 9500 and a total number average molecular weight of 65,000 to 95,000, the weight ratio may range from 60:40 to 90:10, preferably 80:20 to 90:10.

The base block copolymer must have a sufficient molecular weight and polystyrene content to be useful for pressure sensitive adhesives. Generally, the number average molecular weight should be from 65,000 to 300,000. If the molecular weight is less than 65,000 then the polymer loses its pressure sensitive adhesive properties. If the molecular weight is more than 300,000, then the polymer is less useful for adhesive applications. The polystyrene content ranges from 11 to 40% by weight, 19 to 40% for the lower molecular weight (65,000 to 95,000) polymers because this confers the right balance of cohesion and processability to the polymer.

If the polystyrene block number average molecular weight is 20,000 or lower, then the tackifying resin which is used in the adhesive composition must have an aromaticity wherein the MMAP cloud point is at least 45° C. If the polystyrene block molecular weight of the block copolymer is greater than 20,000, then the tackifying resin must have an aromaticity wherein the MMAP cloud point is at least 70° C. If these aromaticity parameters are not satisfied, blends of the polymer, interpolymer and the tackifying resin are not phase table, especially when aged for a few days at elevated temperature.

It is known that one method to characterize tackifying resin compatibility is by determination of cloud points in suitable solvent systems. From the cloud point values obtained, the resin may be characterized as being aliphatic, aromatic, or a combination of both, polar or nonpolar, and having a high or low molecular weight. Hydrocarbon resins display wide variation in cloud point values and thus the cloud point concept is a useful method to characterize hydrocarbon resins.

MMAP cloud point is a well-known measure of aromatic solubility and determines the aliphatic/aromatic character of the resin. The lower the MMAP cloud point value, which is expressed in degrees centigrade, the more aromatic is the resin. A 1:2 mixture of methylcyclohexane and aniline is used as the solvent system in the MMAP cloud point determination. A standard weight of resin is dissolved in the solvent at high temperature and allowed to cool with mixing. The temperature at which the resin begins to separate out as an extra phase is determined to be the cloud point. This may be seen in the mixture as a cloudiness in the previously clear solution.

The viscosity of the adhesive formulation may be lowered by adding to the styrene-diene-styrene block copolymers described above from 5 to 40 percent by weight of a second block copolymer which has a diblock content of 20 to 70 percent by weight. Such block copolymers are often produced by making diblocks and then coupling them together. If the coupling efficiency is less than 100 percent, then the polymer will contain a certain amount of diblock. This is well known to those of ordinary skill in the art.

The viscosity of adhesive composition may also be lowered in the case where the styrene-diene-styrene block copolymer has a polystyrene content of more than 25 percent by weight, preferably 30 percent or more by weight, by adding to that block copolymer from 5 to 40 percent by weight of a second block copolymer which has a polystyrene content of less than 25 percent by weight, preferably 22 percent by weight or less. Also, the viscosity may be lowered by adding more than two styrenic block copolymers.

The second key component of the adhesive formulation of the present invention is the homogeneous linear or substantially linear interpolymer of ethylene and a $C_3$–$C_{20}$ alpha olefin. Generally, these interpolymers have a density from 0.850 to 0.910 g/cm³, a melt flow index of 0.1 to 100 dg/min (190° C./2.16kg), preferably 0.1 to 50, more preferably 0.1 to 30, and most preferably 0.1 to 15, and a polydispersity of less than 2.2. The interpolymers may have densities higher than the preferred range as long as the resulting formulation has a viscosity and adhesive properties within the preferred range.

The term interpolymer is used herein to indicate a copolymer or a terpolymer. That is, at least one other comonomer is polymerized with ethylene to make the interpolymer. The homogeneous linear or substantially linear polymer is an ethylene polymer prepared using a constrained geometry or single site metallocene catalyst. By the term homogeneous, it is meant that any comonomer is randomly distributed within a given interpolymer molecule and substantially all of the interpolymer molecules have the same ethylene/comonomer ratio within that interpolymer. The melting peak of homogeneous linear and substantially linear ethylene polymers, as determined by differential scanning calorimetry (DSC), will broaden as the density decreases and/or as the number average molecular weight decreases. However, unlike heterogeneous polymers, when a homogeneous polymer has a melting peak greater than 115° C. (such as is the case of polymers having a density greater than 0.940 g/cm³) such polymers typically do not additionally have a distinct lower temperature melting peak. The homogeneous linear or substantial linear ethylene polymers are characterized as having a narrow molecular weight distribution ($M_w/M_n$). For the linear and substantially linear ethylene polymers, the $M_w/M_n$ is preferably from 1.5 to 2.5, preferably from 1.8 to 2.2.

Substantially linear ethylene polymers are homogeneous polymers having long chain branching. The long chain branches have the same comonomer distribution as the polymer backbone and can be as long as about the same length as the length of the polymer backbone. When a substantially linear ethylene polymer is employed in the practice of the invention, such polymer will be characterized as having a polymer backbone substituted with from 0.1 to 3 long chain branches per 1000 carbons. Methods for determining the amount of long chain branching present, both qualitatively and quantitatively, are known in the art. For qualitative and quantitative methods for determination, see U.S. Pat. Nos. 5,272,236 and 5,278,272 which are herein incorporated by reference.

The homogeneous linear or substantially linear ethylene polymer will be an interpolymer of ethylene with at least one alpha olefin. Preferred are interpolymers of ethylene with at least one $C_3$–$C_{20}$ alpha olefin (for instance, propylene, isobutylene, 1-butene, 1-pentene, 1-hexene, 4-methyl-1-pentene, and 1-octene) with interpolymers of ethylene with at least one $C_4$–$C_{20}$ alpha olefin, particularly at least one $C_6$–$C_8$ alpha olefin, being most preferred. When 1-octene is employed as the comonomer, preferably the 1-octene is present in an amount greater than 14 percent by weight in the polymer as measured by NMR in accordance with ASTM D-5017. More preferably, the 1-octene comonomer content is greater than 20 percent by weight.

Homogeneously branched linear ethylene/alpha olefin interpolymers may be prepared by using polymerization processes which provide a homogeneous short chain branching distribution. For instance, see U.S. Pat. No. 3,645,992 which is herein incorporated by reference. In this process, a soluble vanadium catalyst system is used. Others have used so-called single site metallocene catalyst systems to make such polymers. Substantially linear ethylene/alpha olefin interpolymers are available from the Dow Chemical Company and may be prepared in accordance with the techniques described in U.S. Pat. Nos. 5,272,236 and 5,278,272 which are herein incorporated by reference.

Suitable tackifiers may be selected from the group consisting of compatible $C_5$ hydrocarbon resins, hydrogenated $C_5$ hydrocarbon resins, styrenated $C_5$ resins, styrenated $C_5/C_9$ resins, styrenated terpene resins, fully hydrogenated or partially hydrogenated $C_9$ hydrocarbon resins, rosins esters, rosins derivatives and mixtures thereof. Of course, the tackifying resin must satisfy the MMAP requirements discussed above. Commercially available hydrocarbon tackifying resins for the present invention include PICCOTAC® 95 (MMAP=95° C.) as aliphatic resin, REGALREZ® series, like REGALREZ® 1085 (85° C.) or REGALREZ® 6108 (54° C.) and REGALITE® series, like REGALITE® V-1100 (48° C.) or REGALITE® S-260 (59° C.). REGALREZ® 3102 resin (MMAP=24° C.) does not work with any of these polymers because a phase stable blend cannot be achieved.

The suitable combination of resin type, block copolymer type, interpolymer type, and rubber concentration in the formulation is required to obtain an easy, fast and homogeneous blend. For example, KRATON® G-1650, a medium molecular weight polymer with 30 percent polystyrene content, can be easily mixed in a Z-blade mixer with PICCOTAC® 95, an aliphatic hydrocarbon resin. RP-6917, a high molecular weight polymer with 33 percent polystyrene content can easily and quickly be homogeneously blended with REGALITE® V-1100. In this case, the aromaticity of the resin helps to dissolve the polymer. However, this blend is not phase stable when aged for several days at elevated temperature. An aliphatic resin, like PICCOTAC® 95 or a hydrogenated pure aromatic resin containing low level of aromaticity like REGALREZ® 1085 can be used to get homogeneous blends.

Suitable plasticizers include plasticizer oils include low aromatic content (carbon aromatic distribution <5%, preferably <2%, more preferably 0% as determined according to DIN 51378) hydrocarbon oils that are paraffinic or naphthenic in character. Those products are commercially available from Shell Oil Company, like SHELLFLEX®, CATENEX®, ONDINA® oils, KAYDOL® oil from Witco, or TUFFLO® oils from Arco. Other plasticizers include compatible liquid tackifying resins like REGALREZ® R-1018. Other ingredients might also be added, like olefin oligomers, low molecular weight polymers like polybutene or liquid polyisoprene, like liquid styrene/isoprene copolymers or hydrogenated styrene/isoprene copolymers, liquid alpha olefin polymers, vegetable oils and their derivatives, paraffin and microcrystalline waxes.

It is known in the art that various other components can be added to modify the tack, the odor, the color of the adhesives. Antioxidants and other stabilizing ingredients can also be added to protect the adhesive from degradation induced by heat, light and processing or during storage. Several types of antioxidants can be used, either primary antioxidants like hindered phenols or secondary antioxidants like phosphite derivatives or blends thereof. Examples of commercially available antioxidants are IRGANOX® 565 from Ciba-Geigy (2.4-bis-(n-octylthio)-6-(4-hydroxy-3,5-di-tertiary-butyl anilino)-1,3,5-triazine), IRGANOX® 1010 from Ciba-Geigy (tetrakis-ethylene-(3,5-di-tertiary-butyl-4-hydroxy-hydrocinnamate)methane) and POLYGUARD® HR from Uniroyal (tris-(2,4-di-tertiary-butyl-phenyl) phosphite).

The adhesive composition of the present invention preferably has a viscosity of 100 to 10,000 cPs at 177° C., preferably from 600 to 6,000 cPs at 177° C. The adhesive typically exhibits no transfer after being peeled away from a fabric. The adhesive composition is used in articles such as disposable diapers, sanitary napkins, bed pads, incontinent pads, surgical drapes, plasters, bandages, and the like.

EXAMPLES

All molecular weights specified in these examples are number average. KRATON G-1650 is a hydrogenated styrene-butadiene-styrene block copolymer having a molecular weight of 109,000, a polystyrene content of 30 percent by weight, and polystyrene block molecular weight of 10,100. RP-6917 is a similar hydrogenated block copolymer having a molecular weight of 286,000, a polystyrene content of 33 percent by weight, and a polystyrene block molecular weight of 29,000. Two different types of metallocene interpolymers were tested, an ethylene-butene-1 copolymer (sold under the trademark EXACT®) and several ethylene/octene-1 copolymers (sold under the trademark ENGAGE®. The table below shows the properties of these polymers. $M_n$ is the number average molecular weight, $M_w$ is the weight average molecular weight, $M_w/M_n$ is a measure of the polydispersity, and MFI is the melt flow index expressed in dg/min at 190° C./2.16kg. Several hydrocarbon tackifying resin types were also evaluated.

| Grade | density g/cm³ | MFI dg/min | $M_n$ | $M_w$ | $M_w/M_n$ |
|---|---|---|---|---|---|
| Engage 8100 | 0.87 | 1 | 103,557 | 179,704 | 1.735 |
| Engage 8200 | 0.87 | 5 | 65,696 | 122,262 | 1.861 |
| Engage 8400 | 0.87 | 30 | 39,930 | 82,881 | 2.076 |
| Exact 4049 | 0.873 | 4.5 | 57,005 | 122,743 | 2.153 |

Example 1

Adhesive Properties of KRATON G-1650 and RP-6917 With ENGAGE 8400

All the ingredients were compounded in a Z-blade mixer. Then the samples were put in beaker in an oven at 180° C. Once molten, the adhesive was poured onto a Mylar sheet and cast to obtain a thickness of 2 mils (50 microns). Prior to testing, the samples were conditioned at 23° C. −50% RH (relative humidity) for 24 hours.

Standard peel, tack and cohesion tests were carried out on these formulations. To assess the right functionality of the adhesive, specific adhesion tests on fabrics were performed, namely to evaluate the adhesion of the positioning adhesive onto the undergarment. Cotton and nylon fabrics are the two reference materials used in these tests.

The following peel adhesion tests on fabric were carried out:

Peel adhesion initial: for cotton, the initial peel is preferred to be in the range of 200–500 g/lineal inch.

Peel adhesion retention or aging test: the samples (fabric/adhesive/Mylar) are put in an oven at 40° C./8 hours under a load of 160 g/sq. in. Peel adhesion is determined after 1 hour conditioning at 23° C. −50R.H. Occurrence of adhesive transfer is also reported as none or transfer.

Adhesive transfer: the samples (fabric/adhesive/Mylar) are put in oven at 40° C./24 hours under a load of 800 g/sq. in. Peel adhesion is determined after 1 hour conditioning at 23° C. −50% R.H. Occurrence of adhesive transfer is also reported as none or transfer.

The SAFT (shear adhesion failure temperature) was measured by 1"×1" Mylar to Mylar lap joint with a 1 kg weight. SAFT measures the temperature at which the lap shear assembly fails under load. Rolling Ball Tack (RBT) is the distance a steel ball rolls on the adhesive film with a standard initial velocity (Pressure Sensitive Tape Council Test No. 6). Small numbers indicate aggressive tack. Holding Power (HP) is the time required to pull a standard area (½ in.×½ in.) of tape from a standard test surface (steel, Kraft paper) under a standard load (1 kg), in shear at 20 (Pressure Sensitive Tape Council Method No. 7). Long times indicate high adhesive strength. 1800 peel was determined by Pressure Sensitive Tape Council Method No. 1. Large numbers indicate high strength when peeling a test tape from a steel substrate. Polyken probe tack (PPT) was determined by ASTM D-2979. Loop tack (LT) was determined using PSTC-5 loop tack method. High numbers for PPT and LT indicate aggressive tack. T-peel is measured by ASTM D-1876.

Table 1 below shows the results for G-1650 and RP-6917 (F-1, F-4) and for KRATON G/ENGAGE 8400 in the other columns (F-2, F-3, F-5, F-6). PICCOTAC® 95 is a trademark for an aliphatic hydrocarbon tackifying resin which is manufactured by Hercules. V-1100 is a hydrogenated mixed cyclic aromatic tackifying resin which is manufactured by Hercules. TUFFLO® 6056 oil is a plasticizing oil which is manufactured by ARCO.

TABLE 1

| Formulation | F-1 | F-2 | F-3 | F-4 | F-5 | F-6 |
|---|---|---|---|---|---|---|
| G1650 | 100 | 75 | 50 | | | |
| RP6917 | | | | 100 | 75 | 50 |
| E-8400 | | 25 | 50 | | 25 | 50 |
| Piccotac 95 | 349 | 349 | 349 | | | |
| V-1100 | | | | 464 | 464 | 464 |
| Tufflo 6056 | 183 | 183 | 183 | 276 | 276 | 276 |
| Irganox 1010 | 3 | 3 | 3 | 3 | 3 | 3 |
| Hot Melt Visc. cPs | 1,830 | 1,185 | 1,025 | 4200 | 1243 | 760 |
| 180 Peel (steel) pli | 4.7 | 3.5 | 5.1 | 2.8 | 6.8 | 3.6 |
| 180 Peel Failure | Ghosting | Ghosting | Cohesive | Cohesive | Cohesive | Cohesive |
| HP Steel, 1 kg (min) | 39 | 14 | 12 | 391 | 72 | 7 |
| | A/G | PA | Cohesive | PC | Cohesive | Cohesive |
| SAFT Mylar 0.5 kg | 67 | 52 | 42 | 65 | 57 | 39 |
| Loop Tack oz/in | 42 | 105 | 120 | 101 | 123 | 128 |
| Adhesion initial | | | | | | |
| T-Peel (cotton) pli | 0.5 | 0.6 | 0.7 | 1.2 | 1.5 | 2.3 T |
| T-Peel (cotton) g | 225 | 270 | 310 | 540 | 680 | 1,040 T |
| T-Peel (nylon) pli | 0.8 | 0.6 | 0.9 | 1.4 | 1.3 | 2.5 T |
| T-Peel (nylon) g | 360 | 270 | 410 | 630 | 580 | 1130 |
| Retention | | | | | | |
| Aged T-Peel (cotton) pli | 0.34 | 0.5 | 0.6 | | 2 | 1.4 T |
| Aged T-peel (cotton) g | 150 | 225 | 270 | | 905 | 630 |
| Aged T-Peel (nylon) pli | 0.7 | 0.7 | 1 | | 1.2 | 1.7 T |
| Aged T-peel (nylon (g) | 310 | 310 | 450 | | 540 | 770 |
| Transfer | | | | | | |
| T-Peel (cotton) pli | 0.81 | | 1.04 | 1.42 | | |
| T-peel (cotton) g | 360 | | 470 | 640 | | |

TABLE 1-continued

| Formulation | F-1 | F-2 | F-3 | F-4 | F-5 | F-6 |
|---|---|---|---|---|---|---|
| T-Peel (nylon) pli | 1.05 |  | 1.34 | 1.28 |  |  |
| T-peel (nylon (g) | 470 |  | 606 | 580 |  |  |

T = transfer
A/G = adhesive/ghosting
PA = partial adhesive
PC = partial cohesive

G-1650/ENGAGE 8400

Comparison of F-1, 2 and 3 indicates that the se of up to 50% of the metallocene interpolymer does not change the adhesion properties on fabric. Indeed, adhesion initial, retention, and transfer are almost equivalent. Hot melt viscosity, holding power, and SAFT are lower than without the interpolymer. The decrease in hot melt viscosity is very attractive because of the trend to go for lower application temperature systems. The decrease in holding power and SAFT is not considered desirable, although no transfer was observed in our testing conditions.

RP-6917/ENGAGE 8400

Comparison of F-4, 5 and 6 indicates that at 50/50 ratio RP-6917/ENGAGE 8400, there is adhesive transfer on fabric, even without aging but not at a ratio 75/25. Other properties, like hot melt viscosity, holding power, and SAFT are lower than without the interpolymer. Thus, smaller amounts of the interpolymer can be used with the KRATON RP-6917 but not as much as with G-1650.

Transfer test

For all the transfer tests on fabric, the peel adhesion profile on cotton is always smoother than that on nylon. This is particularly obvious when the peel adhesion is below about 1 pli (450 g) and when no transfer or very slight transfer is observed.

Example 2

Adhesive Properties of RP-6917 and Engage 8400 With Different Tackyfying Resin This series of test shows that the type of resin used in the formulation influences greatly the end properties. Indeed, F-8, compounded with a R-6108, hydrogenated pure aromatic resin, gives much better properties than F-7, compounded with a mixed cyclic/aromatic resin, V-1100. There is no transfer and the adhesion on fabric is excellent. Compared to F-3, SAFT and holding power are equivalent. After about 4 days storage at 177° C., Formulation F-8 (RP-6917/Engage 8400) shows phase separation. However, the same formulation, compounded either with an aliphatic hydrocarbon resin, like PICCOTAC® 95, or an hydrogenated aromatic resin, like REGALREZ® 1085, does not show phase separation when submitted to the same test. This indicates that a careful selection of the appropriate resins, with the right balance in aliphatic/aromatic character, is needed to achieve the best compatibility between all the ingredients.

TABLE 2

| Formulation | F-7 | F-8 |
|---|---|---|
| RP6917 | 50 | 50 |
| E-8400 | 50 | 50 |
| R-6108 |  | 464 |
| V-1100 | 464 |  |
| Tufflo 6056 | 276 | 276 |
| Irganox 1010 | 3 | 3 |
| Hot Melt Visc. cPs | 760 | 1,593 |
| 180 Peel (steel) pli | 3.6 | 3.6 |
| 180 Peel Failure | Cohesive | Cohesive |
| HP Steel, 1 kg (min) | 7 | 13 |
| HP failure | Cohesive | Cohesive |
| SAFT Mylar 0.5 kg | 39 | 40 |
| Loop Tack oz/in | 128 | 136 |
| Adhesion initial |  |  |
| T-Peel (cotton) pli | 2.3 T | 0.9 |
| T-Peel (cotton) g | 1,040 T | 400 |
| T-Peel (nylon) pli | 2.5 T | 0.9 |
| T-Peel (nylon) g | 1,130 | 400 |
| Retention |  |  |
| Aged T-Peel (cotton) pli | 1.4 T | 0.9 |
| Aged T-peel (cotton) g | 630 | 400 |
| Aged T-Peel (nylon) pli | 1.7 T | 0.9 |
| Aged T-peel (nylon (g) | 770 | 400 |
| Transfer |  |  |
| T-Peel (cotton) pli |  | 0.8 |
| T-peel (cotton) g |  | 360 |
| T-Peel (nylon) pli |  | 0.9 |
| T-peel (nylon (g) |  | 400 |

T = transfer

Example 3

Adhesive Properties of Kraton G-1650 With Engage 8400, Engage 8200, Engage 8100 Blends This series of test has been done to assess the influence of the melt flow index and the molecular weight of the Engage grades on the adhesive properties of positioning adhesives. By replacing part by part Engage 8400 by other Engage grades which have a lower melt flow index, it can be seen that again, the adhesion properties are not affected, but the hot melt viscosity, the SAFT and the holding power increased as expected because the molecular weight of the Engage grades is also increased.

TABLE 3

| Formulation | F-9 | F-19 | F-11 |
|---|---|---|---|
| G1650 | 50 | 50 | 50 |
| E-8400 | 50 |  |  |
| E-8200 |  | 50 |  |
| E-8100 |  |  | 50 |
| Piccotac 95 | 349 | 349 | 349 |

TABLE 3-continued

| Formulation | F-9 | F-19 | F-11 |
|---|---|---|---|
| Tufflo 6056 | 183 | 183 | 183 |
| Irganox 1010 | 3 | 3 | 3 |
| Hot Melt Visc. cPs 177° C. | 1,025 | 2,160 | 4,190 |
| 180 Peel (steel) | 5.1 | 6.4 | 5.5 |
| 180 Peel Failure | Cohesive | Cohesive | Ghosting |
| HP Steel, 1 kg (min) | 12 | 14 | 22 |
| HP Failure | Cohesive | Cohesive | Cohesive |
| SAFT Mylar 0.5 kg | 42 | 41 | 48 |
| Loop Tack oz/in | 120 | 110 | 111 |
| Adhesion initial | | | |
| T-Peel (cotton) pli | 0.7 | 0.6 | 0.6 |
| T-peel (cotton) g | 310 | 270 | 270 |
| T-Peel (nylon) pli | 0.9 | 0.8 | 0.8 |
| T-peel (nylon) g | 400 | 360 | 360 |
| Retention | | | |
| Aged T-Peel (cotton) pli | 0.6 | 0.8 | 0.6 |
| Aged T-peel (cotton) g | 270 | 360 | 270 |
| Aged T-Peel (nylon) pli | 1 | 0.8 | 0.8 |
| Aged T-peel (nylon) g | 450 | 360 | 360 |
| Transfer | | | |
| T-Peel (cotton) pli | 1.04 | | |
| T-peel (cotton) g | 470 | | |
| T-Peel (nylon) pli | 1.04 | | |
| T-peel (nylon) g | 470 | | |

Example 4

Adhesive Properties of G-1650 and Exact 4049

This series compare the adhesive properties obtained with the addition of ethylene/butene-1 copolymer, exact 4049. All the adhesive properties look good, particularly the absence of any transfer on fabric.

TABLE 4

| Formulation | F-12 | F-13 |
|---|---|---|
| G1650 | 100 | 50 |
| E-4049 | | 50 |
| Piccotac 95 | 349 | 349 |
| Tufflo 6056 | 183 | 183 |
| Irganox 1010 | 3 | 3 |
| Hot Melt Visc. cPs 177° C. | 1,830 | 3,245 |
| 180 Peel (steel) pli | 4.7 | 5 |
| 180 Peel Failure | Ghosting | Ghosting |
| HP Steel, 1 kg (min) | 39 | 27 |
| | A/G | Cohesive |

TABLE 4-continued

| Formulation | F-12 | F-13 |
|---|---|---|
| SAFT Mylar 0.5 kg | 67 | 40 |
| Loop Tack oz/in | 42 | 135 |
| Adhesion initial | | |
| T-Peel (cotton) pli | 0.5 | 0.6 |
| T-Peel (cotton) g | 225 | 270 |
| T-Peel (nylon) pli | 0.8 | 0.8 |
| T-Peel (nylon) g | 360 | 360 |
| Retention | | |
| Aged T-Peel (cotton) pli | 0.34 | 0.7 |
| Aged T-peel (cotton) g | 150 | 310 |
| Aged T-Peel (nylon) pli | 0.7 | 1 |
| Aged T-peel (nylon) (g) | 310 | 450 |
| Transfer | | |
| T-Peel (cotton) pli | 0.81 | 1 |
| T-peel (cotton) g | 360 | 450 |
| T-Peel (nylon) pli | 1.05 | 1.1 |
| T-peel (nylon) (g) | 470 | 450 |

Example 5-Comparative Example

The same tests were carried out with four other block copolymers. The first is KRATON G 1652 polymer which has a molecular weight of 79,000, polystyrene block molecular weight of 7100, and polystyrene content of 30 percent by weight. RP6919 polymer is a radial polymer having two hydrogenated styrene-butadiene arms and two unhydrogenated isoprene arms. The molecular weight is 187,000, the polystyrene block molecular weight is 11,500, and the polystyrene content 18 percent. G1726 polymer is an SEBS polymer having a molecular weight of 73,000, a polystyrene block molecular weight of 7100, a polystyrene content of 31 percent, and which has a coupling efficiency of 30 percent (this means that only percent of the total polymer is triblock and the rest is diblock). The fourth polymer is SEPTON 4033 polymer made by Kuraray (hydrogenated styrene-isoprene-styrene, SEPS) which has a molecular weight of 96,000, a polystyrene block molecular weight of 8100, and a polystyrene content of 28 percent by weight. 1652 was not acceptable at a 50:50 weight ratio (F-14) but the formulation at 85:15 1652:E-8400 (F-19) worked well. It can be seen that neither the 1726 (F-16) nor the 6919 (F-17) used alone are acceptable because they produce adhesives which transfer to the fabric. However, the blend of 1652 and 1726 (F-20) worked well. SEPTON 4033 is acceptable because the properties are good and there is no transfer.

TABLE 5

| Formulation | F-1 | F-14 | F-15 | F-16 | F-17 | F-18 | F-19 | F-20 |
|---|---|---|---|---|---|---|---|---|
| G-1650 | 50 | | | | | | | 60 |
| ENGAGE 8400 | 50 | 50 | | 50 | 50 | 50 | 15 | 25 |
| Exact 4049 | | | 50 | | | | — | — |
| G-1652 | | 50 | 50 | | | | 85 | — |
| G-1726 | | | | 50 | | | — | 15 |
| RP-6919 | | | | | 50 | | — | — |
| Septon 4033 | | | | | | 50 | — | — |
| Piccotac 95 | 349 | 349 | 349 | 349 | 349 | 349 | 349 | 349 |
| Tufflo 6056 | 183 | 183 | 183 | 183 | 183 | 183 | 183 | 183 |
| Irganox 1010 | 3 | 3 | 3 | 3 | 3 | 3 | 3 | 3 |
| Hot Melt Visc cPs 177° C. | 1,025 | 620 | 1,450 | 159 | 644 | 898 | 590 | 638 |
| 180° Peel (steel) pli | 5.1 | 4.9 | 7.8 | 3 | 4.1 | 4.7 | — | — |
| 180° Peel Failure | cohesive | cohesive | cohesive | cohesive | cohesive | cohesive | — | — |

TABLE 5-continued

| Formulation | F-1 | F-14 | F-15 | F-16 | F-17 | F-18 | F-19 | F-20 |
|---|---|---|---|---|---|---|---|---|
| HP Steel, 1 kg (min) | 12 | 12 | 61 | 0.8 | 1 | 6 | — | — |
| HP Failure | cohesive | cohesive | cohesive | cohesive | cohesive | cohesive | — | — |
| SAFT Mylar 0.5 kg | 42 | 40 | 40 | 40 | 39 | 39 | — | — |
| Loop Tack oz/in | 120 | 142 | 155 | 96 | 192 | 119 | — | — |
| Adhesion initial | | | | | | | | |
| T-Peel (cotton) pli | 0.7 | 0.5 | 0.8 | 1.3 ST | 1.5 T | 0.5 | 0.6 | 0.8 |
| T-Peel (cotton) g | 310 | 225 | 360 | 580 ST | 680 T | 225 | 270 | 360 |
| T-Peel (nylon) pli | 0.9 | 0.7 | 0.9 | 1.2 ST | 1.5 T | 1 | 0.3 | 0.5 |
| T-Peel (nylon) g | 410 | 310 | 400 | 540 ST | 680 T | 450 | 150 | 225 |
| Retention | | | | | | | | |
| Aged T-Peel (cotton) pli | 0.6 | 2.2 T | 4 T | | 1.6 T | 1.3 | 0.7 | 0.8 |
| Aged T-Peel (cotton) g | 270 | 990 T | 1800 | | 724 T | 580 | 310 | 360 |
| Aged T-Peel (nylon) pli | 1 | 2.9 T | 2.2 T | | 1.7 T | 1.5 | 0.7 | 0.9 |
| Aged T-Peel (Nylon) g | 450 | 1300 T | 990 | | 770 T | 680 | 310 | 410 |
| Transfer | | | | | | | | |
| 24 hr. T-Peel (cotton) pli | 1.04 | | | | | 1.3 | 1.2 | 0.9 |
| 24 hr. T-Peel (cotton) g | 470 | | | | | 580 | 540 | 410 |
| 24 hr. T-Peel (nylon) pli | 1.34 | | | | | 1.5 | 1.2 | 1 |
| 24 hr. T-Peel (nylon) g | 606 | | | | | 680 | 540 | 450 |

Example 6

In this example, blends of various tackifying resins with varying MMAP values were tested with several block copolymers and interpolymers for phase stability. The results are shown in Table 6 below.

TABLE 6

Compatibility SBC/resin/metallocene blends in function of the aromaticity of the resin as defined by the MMAP cloud point

| | R-3102 | V-1100 E-8400 | R-6108 E-8400 | R-1085 E-4049 | PICCOTAC 95 E-4049 |
|---|---|---|---|---|---|
| MMAP ° C. | 24 | 48 | 54 | 85 | 95 |
| G-1650 | I | C | — | C | C |
| RP-6917 | I | I | I | C | C |

I = INCOMPATIBLE
C = COMPATIBLE

Example 7

In this experiment, two blends of the block copolymer and interpolymer were compared with the neat block copolymer in respect of their viscosity/temperature profiles. It can be seen from the results shown in Table 7 below that both of the blends are lower in viscosity at lower temperatures. This is precisely the desired advantage so that the adhesives containing them can be more easily processed at lower temperatures.

TABLE 7

| Temperature ° F. | G-1650-15.7% | G-1650/E-8400 | G-1650/E-4049 |
|---|---|---|---|
| 275 | 73,300 | 11,075 | 37,800 |
| 300 | 16,240 | 4,600 | 14,480 |
| 325 | 4,570 | 1,985 | 6,760 |
| 350 | 1,800 | 1,039 | 3,245 |

Example 8

The same tests were carried out with four other polymers. Polymer C is a styrenic block copolymer which has a molecular weight of 79,000, a polystyrene block molecular weight of 7100, a polystyrene content of 30 percent by weight and a butylene content of about 70%. RP-6924 is a styrenic block copolymer which has a molecular weight of 140,000, a polystyrene block molecular weight of 10,000, a polystyrene content of 20 percent by weight and a butylene content of about 70%. Polymer D is a styrenic block copolymer which has a molecular weight of 148,000, a polystyrene block molecular weight of 7,400, a polystyrene content of 16 percent by weight, and a butylene content of about 70%. G-1657 is a styrenic block copolymer which has a molecular weight of 148,000, a polystyrene block molecular weight of 5,300, a polystyrene content or 13 percent by weight, and a diblock content of 35 percent by weight. Polymer C (Formulation F-21) and Polymer D (Formulation F-24) show good peel adhesion properties on cotton and nylon without adhesive transfer onto these fabrics for a ratio polymer/polyolefin 15/85% by weight. At another ratio, namely 50/50% by weight, Formulation F-22, the formulation shows adhesive transfer. However, RP-6924 at a ratio of 50/50% by weight shows good peel adhesion on cotton and nylon without adhesive transfer onto these fabrics. G-1657 based formulations (Formulations F-25 and F-26) show adhesive transfer on cotton and nylon and fail for this test.

TABLE 8

| Ingredients | F-21 | F-22 | F-23 | F-24 | F-25 | F-26 |
|---|---|---|---|---|---|---|
| Polymer C | 15 | 50 | | | | |
| G-6924 | | | 50 | | | |
| Polymer D | | | | 15 | | |
| G-1657 | | | | | 15 | 50 |
| Engage 8200 | 85 | 50 | 50 | 85 | 85 | 50 |
| Piccotac 95 | 349 | 349 | 349 | 349 | 349 | 349 |
| Ondina 68 | 183 | 183 | 183 | 183 | 183 | 183 |
| Irganox 1010 | 3 | 3 | 3 | 3 | 3 | 3 |
| Properties | | | | | | |
| Adhesion Initial | | | | | | |
| T-Peel Cotton N/m | 45 | 95 | 60 | 60 | 85 | 100 |
| T-Peel Nylon N/m | 155 | 195 | 120 | 125 | 155 | 175T |

TABLE 8-continued

| Ingredients | F-21 | F-22 | F-23 | F-24 | F-25 | F-26 |
|---|---|---|---|---|---|---|
| Retention | | | | | | |
| T-Peel Cotton N/m | 170 | 560T | 140 | 180 | 190 | 500T |
| T-Peel Nylon N/m | 290 | 400 | 240 | 320 | 310 | 520T |
| Transfer | | | | | | |
| T-Peel Cotton N/m | 275 | 640T | 390 | 330 | 560T | 560T |
| T-Peel Nylon N/m | 360 | 640T | 350 | 380 | 390 | 560T |

T = Adhesive transfer onto fabric

Example 9

In this experiment, blends of block copolymer with elevated butylene and interpolymer Engage 8200 were compared with the neat block copolymer in respect of their viscosity/temperature profile. It can be seen in Table 9 that the reported viscosities are low. It should also be recognized that the formulation F-19 that contains a blend KRATON® G-1650/Engage 8200 has a hot-melt viscosity of 2160 at 177° C., higher than those reported in Table 9 for the same temperature.

TABLE 9

| Temperature | Engage 8200/ P-5828 cPs | Engage 8200/ P-6924 cPs | Engage 8200/ P-7297 cPs |
|---|---|---|---|
| 120° C. | 14,000 | 26,300 | 13,300 |
| 140° C. | 5,600 | 6,360 | 5,540 |
| 160° C. | 2,820 | 1,800 | 2,690 |
| 177° C. | 1,700 | 960 | 1,620 |

We claim:

1. A hot melt pressure sensitive positioning adhesive for use with an absorbent article which comprises:
  (a) from 5 to less than 15 percent by weight, basis the total of (a), (b), and (c), of a blend of
    (i) a hydrogenated styrene(butadiens and/or isoprene)-styrene block copolymer having a polystyrene block number average molecular weight of above 9,500 to 20,000, and
    (ii) a homogeneous linear or substantially linear interpolymer of ethylene and at least one $C_3$–$C_{20}$ alpha oletin having a density from 0.85 to 0.91 grams per cubic centimeter; and
  (b) from 50 to 80 percent by weight, basis the total of (a), (b), and (c), of a tackifying resin which has an aromaticity such that the MMAP cloud point is at least 45° C.; and from 5 to 35 percent by weight, basis the total of (a), (b), and (c), of a plasticizing oil.

2. The adhesive of claim 1 wherein the blend of (a) contains a block copolymer having a total molecular weight of above 95,000 to 300,000 and interpolymer in a weight ratio of from 90:10 to 10:90.

3. The adhesive of claim 2 wherein the blend of (a) contains said block copolymer and interpolymer in a weight ratio of from 80:20 to 20:80.

4. The adhesive of claim 3 wherein the blend of (a) contains block copolymer and interpolymer in a weight ratio of from 60:40 to 40:60.

5. The adhesive of claim 1 wherein the block copolymer of (i) also contains from 5 to 40 percent by weight of a second block copolymer which has a diblock content of 20 to 70 percent by weight.

6. The adhesive composition of claim 1 wherein the block copolymer of (i) has a polystyrene content of more than 25 percent by weight and has added to it from 5 to 40 percent by weight of a second block copolymer having a polystyrene content of less than 25 percent by weight.

7. The adhesive of claim 6 wherein the polystyrene content of the second block copolymer is 22 percent by weight or less.

8. A hot melt pressure sensitive positioning adhesive for use with an absorbent article which comprises:
  (a) from 5 to less than 15 percent by weight, basis the total of (a), (b), and (c), of a blend of
    (i) a hydrogenated styrene-(butadiene and/or isoprene)-styrene block copolymer having a polystyrene block number average molecular weight of greater than 20,000, and
    (ii) a homogeneous linear or substantially linear interpolymer of ethylene and at least one $C_3$–$C_{20}$ alpha olefin having a density from 0.85 to 0.91 grams per cubic centimeter; and
  (b) from 50 to 80 percent by weight, basis the total of (a), (b), and (c), of a tackifying resin which has an aromaticity such that the MMAP cloud point is at least 70° C.; and
  (c) from 5 to 35 percent by weight, basis the total of (a), (b), and (c), of a plasticizing oil.

9. The adhesive of claim 8 wherein the blend of (a) contains block copolymer and interpolymer in a weight ratio of from 90:10 to 10:90.

10. The adhesive of claim 9 wherein the blend of (a) contains block copolymer and interpolymer in a weight ratio of from 80:20 to 20:80.

11. The adhesive of claim 10 wherein the blend of (a) contains block copolymer and interpolymer in a weight ratio of from 60:40 to 40:60.

12. The adhesive of claim 8 wherein the block copolymer of (i) also contains from 5 to 40 percent weight of a block copolymer which has a diblock content of 20 to 70 percent by weight.

13. The adhesive composition of claim 8 wherein the block copolymer of (i) has a polystyrene content of more than 25 percent by weight and has added to it from 5 to 40 percent by weight of a second block copolymer having a polystyrene content of less than 25 percent by weight.

14. The adhesive of claim 13 wherein the polystyrene content of the second block copolymer is 22 percent by weight or less.

15. The hot melt adhesive of claim 1 wherein the viscosity of the adhesive is from 100 to 10,000 cPs at 177° C. and the adhesive exhibits no transfer after being peeled away from a fabric.

16. The adhesive of claim 15 wherein the viscosity of the adhesive is from 600 to 6000 cPs at 177° C.

17. The hot melt adhesive of claim 8 wherein the viscosity of the adhesive is from 100 to 10,000 cPs at 177° C. and the adhesive exhibits no transfer after being peeled away from a fabric.

18. The hot melt adhesive of claim 17 wherein the viscosity of the adhesive is from 600 to 6,000 cPs at 177° C. and the adhesive exhibits no transfer after being peeled away from a fabric.

* * * * *

UNITED STATES PATENT AND TRADEMARK OFFICE
CERTIFICATE OF CORRECTION

PATENT NO. : 6,657,000 B1
DATED : December 2, 2003
INVENTOR(S) : Noel Raymond Maurice De Keyzer and Carolyn Ann Stoner It is certified that error appears in the above-identified patent and that said Letters Patent is hereby corrected as shown below:

Column 17,
Lines 36-52, should read:
1. A hot melt pressure sensitive positioning adhesive for use with an absorbent article consisting essentially of:
(a) from 5 to less than 15 percent by weight, basis the total of (a), (b), and (c), of a blend of
    (i) a hydrogenated styrene-(butadiene and/or isoprene)-styrene block copolymer having a polystyrene block number average molecular weight of above 9,500 to 20,000, and
    (ii) a homogeneous linear or substantially linear interpolymer of ethylene and at least one $C_3$-$C_{20}$ alpha olefin having a density from 0.85 to 0.91 grams per cubic centimeter; and
(b) from 50 to 80 percent by weight, basis the total of (a), (b), and (c), of a tackifying resin which has an aromaticity such that the MMAP cloud point is at least 45°C.; and
(c) from 5 to 35 percent by weight, basis the total of (a), (b), and (c), of a plasticizing oil; wherein the adhesive exhibits no transfer after being peeled away from fabric.

Column 18,
Lines 10-28, should read:
8. A hot melt pressure sensitive positioning adhesive for use with an absorbent article consisting essentially of:
(a) from 5 to less than 15 percent by weight, basis the total of (a), (b), and (c), of a blend of
    (i) a hydrogenated styrene-(butadiene and/or isoprene)-styrene block copolymer having a polystyrene block number average molecular weight of greater than 20,000, and
    (ii) a homogeneous linear or substantially linear interpolymer of ethylene and at least one $C_3$-$C_{20}$ alpha olefin having a density from 0.85 to 0.91 grams per cubic centimeter; and
(b) from 50 to 80 percent by weight, basis the total of (a), (b), and (c), of a tackifying resin which has an aromaticity such that the MMAP cloud point is at least 70° C.; and
(c) from 5 to 35 percent by weight, basis the total of (a), (b), and (c), of a plasticizing oil; wherein the adhesive exhibits no transfer after being peeled away from fabric.

UNITED STATES PATENT AND TRADEMARK OFFICE
CERTIFICATE OF CORRECTION

PATENT NO. : 6,657,000 B1
DATED : December 2, 2003
INVENTOR(S) : Noel Raymond Maurice De Keyzer and Carolyn Ann Stoner It is certified that error appears in the above-identified patent and that said Letters Patent is hereby corrected as shown below:

<u>Column 18, (cont.)</u>
Lines 52-53, should read:
15. The hot melt adhesive of claim 1 wherein the viscosity of the adhesive is from 100 to 10,000 cPs at 177° C.
Lines 57-58, should read:
17. The hot melt adhesive of claim 8 wherein the viscosity of the adhesive is from 100 to 10,000 cPs at 177 °C.
Lines 61-62, should read:
18. The hot melt adhesive of claim 17 wherein the viscosity of the adhesive is from 600 to 6,000 cPs at 177 °C.

Signed and Sealed this

Twenty-third Day of March, 2004

JON W. DUDAS
*Acting Director of the United States Patent and Trademark Office*